US005637485A

United States Patent [19]
Jarry et al.

[11] Patent Number: 5,637,485
[45] Date of Patent: *Jun. 10, 1997

[54] PRODUCTION OF ITACONIC ACID BY FERMENTATION

[75] Inventors: Alain Jarry, Maisonnay; Yolaine Seraudie, Melle, both of France

[73] Assignee: Rhone-Poulenc Chimie, Courbevoie Cedex, France

[*] Notice: The term of this patent shall not extend beyond the expiration date of Pat. No. 5,457,040.

[21] Appl. No.: 449,947

[22] Filed: May 25, 1995

Related U.S. Application Data

[62] Division of Ser. No. 205,646, Mar. 4, 1994, Pat. No. 5,457,040.

[30] Foreign Application Priority Data

Mar. 12, 1993 [FR] France ................................. 93 02844

[51] Int. Cl.$^6$ ........................................................... C12P 7/44
[52] U.S. Cl. ................................................ 435/142; 435/913
[58] Field of Search ........................................ 435/142, 913

[56] References Cited

U.S. PATENT DOCUMENTS 3,044,941   7/1962   Nubel et al. .
3,873,425   3/1975   Kobayashi et al. ................. 435/145
4,740,464   4/1988   Holdom et al. ..................... 435/135
5,231,016   7/1993   Cros et al. .......................... 435/142
5,457,040   10/1995  Jarry et al. ......................... 435/142

FOREIGN PATENT DOCUMENTS 0697653   11/1964   Canada ............................. 435/142
0052990   7/1973    Japan ............................... 435/142
133881    7/1985    Japan .
148979    6/1988    Japan .
0507633   3/1976    U.S.S.R. ........................... 435/142
0602866   6/1948    United Kingdom ............... 435/142
0795401   5/1958    United Kingdom ............... 435/142
0878152   9/1961    United Kingdom ............... 435/142

*Primary Examiner*—Herbert J. Lilling
*Attorney, Agent, or Firm*—Burns, Doane, Swecker & Mathis, L.L.P.

[57] ABSTRACT

Itaconic acid and/or salt thereof is produced via aerobic microbial fermentation, for example by means of the species *Aspergillus terreus* or *Aspergillus itaconicus*, of a nutrient medium containing a source of assimilable carbon, such carbon source at least in part comprising an effective amount of glycerol.

6 Claims, No Drawings

PRODUCTION OF ITACONIC ACID BY FERMENTATION

This application is a divisional of application Ser. No. 08/205,646, filed Mar. 4, 1994 now U.S. Pat. No. 5,457,040.

BACKGROUND OF THE INVENTION

1. Field of the Invention

The present invention relates to the preparation of itaconic acid by fermentation, and, more especially, via microbial fermentation of particular nutrient media.

2. Description of the Prior Art

The production of organic acids by fermentation of sugars in the presence of a suitable microorganism is universally known to this art. Typical acids of such fermentations include, in particular, acetic acid, lactic acid, citric acid, fumaric acid and, more especially, itaconic acid.

Itaconic acid is a dicarboxylic acid having the following structural formula:

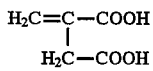

By reason of its site of ethylenic unsaturation, itaconic acid esters polymerize very readily and are thus widely used in the detergent and synthetic plastics industries and in the preparation of adhesives.

Traditionally, the production of itaconic acid is carried out by fermentation. Various varieties of the genus Aspergillus, and more especially those of *Aspergillus terreus* and *Aspergillus itaconicus*, are used for producing itaconic acid via fermentation of carbohydrates.

The carbohydrates most typically used include mono- and disaccharides, such as glucose, sucrose and fructose and starches, as they exist in a form which is assimilable by the microorganism, and molasses.

Indeed, in traditional fermentations, from an economic standpoint, the selection of the hydrocarbon substrate should be based both on its cost, on its availability and on its capacity to provide high yields.

Thus, in order to economically optimize the processes for preparing itaconic acid, it is necessary to select a hydrocarbon source that simultaneously satisfies the aforesaid three requirements.

SUMMARY OF THE INVENTION

Accordingly, a major object of the present invention is the provision of an improved fermentation process, utilizing a unique carbon source which is available in large amounts and at lower cost and which is completely assimilable by the microorganisms suitable for the production of itaconic acid.

Briefly, the present invention features a process for the production of itaconic acid and/or the salts thereof by aerobic fermentation of a carbohydrate via suitable microorganism, and wherein the carbon substrate or source of the nutrient medium at least in part comprises an effective amount of glycerol.

DETAILED DESCRIPTION OF BEST MODE AND PREFERRED EMBODIMENTS OF THE INVENTION

More particularly according to the present invention, it has now unexpectedly been determined that glycerol is fully assimilable by microorganisms that are suitable for the fermentative production of itaconic acid. In comparison with the other carbon substrates indicated above, glycerol presents the distinct advantage of being especially advantageous from an economic standpoint. It is readily available in vast amounts and at very low cost. Its use as the carbon substrate or source provides high yields of itaconic acid at fermentation times comparable to those employed with the traditional carbon substrates.

It will of course be appreciated that the glycerol may be used either alone or mixed with at least one other carbohydrate. The latter may be selected from among, for example, the mono- and disaccharides such as glucose, sucrose and fructose, starches and molasses.

In mixtures of this type, the respective proportions of glycerol and additional carbohydrate(s) can vary widely, with the proviso that the overall amount thereof is sufficient to permit the fermentation process to proceed effectively.

For the formulation of the corresponding nutrient media, it is preferable to employ a concentration of carbon substrate, whether glycerol alone or mixed with one or more other additional carbohydrates, ranging from 10 to 240 g/l expressed in terms of weight/volume.

In one particular embodiment of the invention, the itaconic acid is partially neutralized during the fermentation process, by the addition, for example, of alkali of the sodium hydroxide or potassium hydroxide type. In this particular case, the itaconic acid is obtained mixed with one of its inorganic salts, for example the sodium or potassium salt.

The glycerol may be introduced into the nutrient medium in several ways. Traditionally, it is introduced directly, whether or not with another carbohydrate, into the nutrient medium. However, the glycerol can already be present as the primary carbon substrate in the preparation of the inoculum, or of the preculture of the selected microorganism. This inoculum is transferred in a subsequent step into a nutrient medium to initiate the fermentation. Given this option, the concentration of glycerol, whether or not mixed with another carbohydrate, is supplemented in the nutrient medium to attain the requisite concentration described above.

Particularly exemplary for carrying out the fermentation process of the invention include the species *Aspergillus terreus* and *Aspergillus itaconicus*.

Preferred is the species *Aspergillus terreus*, and preferably the strain NRRL 1960 identified in EP-341,112.

Other than the glycerol according to the invention, the nutrient medium also contains other nutrient ingredients required for fermentation. One skilled in this art can easily select these other ingredients and the respective amounts thereof.

The nitrogen source can, in particular, be selected from among metabolizable organic or inorganic compounds, such as soluble extract of maize (SCL) and/or of soya bean, urea, ammonium sulfate, ammonium chloride, ammonium phosphate, ammonium nitrate and the like, and mixtures thereof.

The medium contains, in addition, inorganic salts such as Ca, Mg, Na, K, Fe, Ni, Co, Cu, Mn, Zn sulfates, chlorides and phosphates, as well as other common additives such as pH regulators and/or antifoams.

The microorganism is itself introduced into the fermentation medium in conventional manner, by means of inoculum or of intermediate cultures.

The fermentation is suitably carried out at an acid pH ranging from approximately 1.8 to 5 and at a temperature of approximately 20° to approximately 40° C., optimal conditions depending on the particular strain of the microorganism employed.

In order to further illustrate the present invention and the advantages thereof, the following specific example is given, it being understood that same are intended only as illustrative and in nowise limitative.

EXAMPLE

The production of itaconic acid was carried out using several nutrient media that differed from one another in the amount of glycerol employed.

The nutrient solution used contained 0.5 g of maize extract (CSL), 1.2 g of ammonium nitrate, 0.3 g of hydrated magnesium sulfate, 0.3 g of magnesium oxide, 0.315 g of calcium hydroxide, 0.05 g of monopotassium phosphate and 0.380 g of hydrated copper nitrate. The total volume of this production medium was adjusted to 1 liter with water, and its pH was adjusted to a value on the order of 2.8 to 3 by means of nitric acid solution.

Depending on the test carried out, this nutrient medium was supplemented with glycerol, mixed or otherwise with sucrose. The respective amounts of each of the carbon substrates are reported in the Table below.

For each test, the above nutrient medium was introduced into a 500 ml Erlenmeyer flask and inoculated with an *Aspergillus terreus* NRRL 1960 culture such as to provide a concentration on the order of $5 \times 10^{-7}$ spores/ml in the medium. The temperature of the medium was adjusted to 32°–35° C.

Fermentation was terminated after the sugar had been exhausted and when the acidity was at a maximum and stable.

Samples of musts were taken at the end of the fermentation to evaluate the itaconic acid content, determined by high performance liquid chromatography.

The productivity of itaconic acid for each test is reported in the Table below.

The results obtained demonstrated that glycerol was a hydrocarbon substrate which was fully assimilable by the microorganism *Aspergillus terreus*, and, hence, suitable for the production of itaconic acid in satisfactory yields.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An improved process for the production of itaconic acid and/or a salt thereof by aerobic microbial fermentation of a nutrient medium containing a source of assimilable carbon and at least one microorganism which produces itaconic acid and/or a salt thereof when cultured in the presence of said assimilable carbon, the improvement wherein said source of assimilable carbon at least in part comprises an effective amount of glycerol and the microorganism is a strain of *Aspergillus terreus* or *Aspergillus itaconicus*.

2. The fermentation process of claim 1 wherein the fermentation medium comprises from 10 to 240 g/l of said source of assimilable carbon.

3. The fermentation process of claim 2 wherein the fermentation medium comprises from about 25 to 100 g/l of glycerol.

4. The fermentation process of claim 2 wherein the microorganism is a strain of *Aspergillus terreus*.

5. The fermentation process as defined by claim 1, said source of assimilable carbon also comprising a carbohydrate.

6. The fermentation process as defined by claim 1, the fermentation medium also comprising a nitrogen source and at least one inorganic salt.

TABLE

| | Carbohydrate Content of the Media | | Acidities (g/l) | | | | | Results at 161 or 233 Hours | | |
|---|---|---|---|---|---|---|---|---|---|---|
| Test No. | Sucrose (g/l) | Glycerol (g/l) | 72 Hours | 96 Hours | 120 Hours | 161 Hours | 233 Hours | Glycerol Remaining (g/l) | Itaconic Acid (g/l) | Molar Yld. % |
| 1 | 75 | 25 | 10.05 | 26 | 42.25 | 55.9 | 64.35 | 5.8 | 57.85 | 80 |
| 2 | 50 | 50 | 7.15 | 21.45 | 35.6 | 48.75 | 60.5 | 8.7 | 57.15 | 80.1 |
| 3 | 25 | 75 | 10.5 | 20.3 | 29.6 | 41.95 | 58.2 | 10.7 | 52.75 | 74.15 |
| 4 | 0 | 100 | 10.25 | 20.5 | 31.0 | 46.65 | 55.9 | 2.9 | 49.6 | 62.8 |
| 5 | 110 | 0 | 19.8 | 38 | 56.55 | 76.7 | — | — | 69.7 | 83.8 |